United States Patent
Meersseman et al.

(10) Patent No.: US 11,827,929 B2
(45) Date of Patent: Nov. 28, 2023

(54) OPTIMIZED CLINICAL SAMPLE SEQUENCING

(71) Applicant: Biocartis, NV, Mechelen (BE)

(72) Inventors: Geert Meersseman, Brussels (BE); Nicolas Vergauwe, Borgloon (BE)

(73) Assignee: BIOCARTIS, NV, Mechelen (BE)

( * ) Notice: Subject to any disclaimer, the term of this patent is extended or adjusted under 35 U.S.C. 154(b) by 271 days.

(21) Appl. No.: 15/578,158

(22) PCT Filed: Jul. 19, 2016

(86) PCT No.: PCT/EP2016/067148
§ 371 (c)(1),
(2) Date: Nov. 29, 2017

(87) PCT Pub. No.: WO2017/013102
PCT Pub. Date: Jan. 26, 2017

(65) Prior Publication Data
US 2018/0245131 A1   Aug. 30, 2018

(30) Foreign Application Priority Data

Jul. 23, 2015 (EP) .................... 15178159

(51) Int. Cl.
| | |
|---|---|
| C12Q 1/686 | (2018.01) |
| G01N 35/00 | (2006.01) |
| C12Q 1/6869 | (2018.01) |
| C12Q 1/6851 | (2018.01) |
| C40B 60/06 | (2006.01) |

(52) U.S. Cl.
CPC ........... C12Q 1/686 (2013.01); C12Q 1/6851 (2013.01); C12Q 1/6869 (2013.01); G01N 35/00029 (2013.01); C40B 60/06 (2013.01); G01N 2035/00158 (2013.01); G01N 2035/00366 (2013.01)

(58) Field of Classification Search
CPC .... C12Q 1/686; C12Q 1/6851; C12Q 1/6869; C12Q 2535/122; C12Q 2545/114; C12Q 2537/143; C04B 60/06; G01N 2035/158; G01N 2035/366; G01N 35/00029; G01N 2035/00158; G01N 2035/00366; C40B 60/06
See application file for complete search history.

(56) References Cited

U.S. PATENT DOCUMENTS

| | | | |
|---|---|---|---|
| 6,168,948 B1 * | 1/2001 | Anderson | B01F 31/86 435/6.12 |
| 6,383,393 B1 | 5/2002 | Colpan | |
| 8,153,372 B2 * | 4/2012 | Allen | C12Q 1/6851 435/6.12 |
| 9,347,100 B2 | 5/2016 | Shoemaker et al. | |
| 9,498,778 B2 | 11/2016 | Corey | |
| 2003/0152974 A1 | 8/2003 | Gauche | |
| 2005/0208539 A1 | 9/2005 | Vann | |
| 2010/0021910 A1 | 1/2010 | Cao | |
| 2013/0203634 A1 * | 8/2013 | Jovanovich | B01L 3/502738 506/26 |
| 2014/0051844 A1 | 2/2014 | Forman | |
| 2018/0243719 A1 | 8/2018 | Meersseman | |
| 2018/0291367 A1 | 10/2018 | Meersseman | |

FOREIGN PATENT DOCUMENTS

| | | | |
|---|---|---|---|
| EP | 1690938 A1 | 8/2006 | |
| EP | 2128169 A1 | 12/2009 | |
| EP | 2345719 A1 | 7/2011 | |
| JP | 2005137298 A | 6/2005 | |
| JP | 2007325562 A | 12/2007 | |
| JP | 2008529509 A | 8/2008 | |
| WO | 2001071732 | 9/2001 | |
| WO | 2004108925 A1 | 12/2004 | |
| WO | 2010145843 A1 | 12/2010 | |
| WO | 2000029563 A1 | 7/2011 | |
| WO | 2012012779 A2 | 1/2012 | |
| WO | 2012024658 A2 | 2/2012 | |
| WO | 2013024072 A1 | 2/2013 | |
| WO | WO-2014082032 A1 * | 5/2014 | ........... C12Q 1/6851 |
| WO | 2014144174 A1 | 9/2014 | |
| WO | WO-2015051888 A1 * | 4/2015 | ........... C12Q 1/6886 |

OTHER PUBLICATIONS

Anderson et al. A miniature integrated device for automated multistep genetic assays. Nucleic Acids Research 2000; 28: e60. (Year: 2000).*
Henegarin et al. Multiplex PCR: Critical Parameters and Step-by-Step Protocol. BioTechniques 1997; 23: 504-511. (Year: 1997).*
Gholami et al. Plant Biotechnology Journal 2012; 10: 635-645 (Year: 2012).*
Traverso et al. Biochemical and Biophysical Research Communications 2006; 339: 145-150 (Year: 2006).*
Didelot et al. Multiplex Picoliter-Droplet Digital PCR for Quantitative Assessment of DNA Integrity in Clinical Samples. Clinical Chemistry 2013; 59: 815-823 (Year: 2006).*
Swango et al. A quantitative PCR assay for the assessment of DNA degradation in forensic samples. Forensic Science International 2006; 158: 14-26 (Year: 2006).*

(Continued)

*Primary Examiner* — David C Thomas
(74) *Attorney, Agent, or Firm* — Quarles & Brady LLP

(57) ABSTRACT

The present invention generally concerns an automated system capable of performing quantitative PCR (qPCR) analysis of a nucleic acid present in a biological sample together with preparation of a sequencing-ready nucleic acid library from the sample, either simultaneously or sequentially. In a further aspect, the present invention also provides a method for performing qPCR of a nucleic acid present in a biological sample together with simultaneous of sequential preparation of a sequencing-ready nucleic acid library from the sample. Finally, the present invention also provides removable cartridges for use in the automated systems and methods according to the invention.

8 Claims, 7 Drawing Sheets
Specification includes a Sequence Listing.

(56) References Cited

OTHER PUBLICATIONS

Xu et al. Lab on a Chip 2010; 10: 3103-3111. (Year: 2010).*
Coulter, Beckman, "SPRIworks Systems", (2011), www.beckmancoulter.com/wsrportal/bibliography?docname=BR-15981.pdf.
Doyle, Ken, "DNA Quantitation in Next-Generation Sequencing Library Workflows", Promega Corporation Web site. http://www.promega.com/resources/pubhub/dna-quantitation-in-next-generation-sequencing-library-workflows/ Feb. 2015, pp. 1-7.
Loewe, Robert P., "Combinational Usage of Next Generation Sequencing and qPCR for the analysis of Tumor Samples", Methods, vol. 59, No. 1, Jan. 2013, pp. 126-131.
Schiefer, Anna-Iris, et al., "Evaluation of a Novel Fully Automated PCR-based Technique for Detection of BRAF-status in FFPE-tissues", medical University of Vienna, Jan. 2014, p. 1.
Sims, David, et al., "High-throughput RNA interference screening using pooled shRNA libraries and next generation Sequencing", Genome Biology, Oct. 2011, vol. 12, No. 10, p. R104.
International Search Report and Written Opinion for PCT/EP2016/067148 dated Oct. 10, 2016.
Buehler, B., et al., "Rapid Quantification of DNA Libraries for Next-Generation Sequencing", Methods, Apr. 2010, vol. 50, No. 4, pp. S15-S18.
Chiu et al., Viral Diagnostics and Discovery by Next-Generation Sequencing, IPFA/PEI International Workshop, Budapest, Hungary, 2012, 1-43. (Year: 2012).
Beckman Coulter, Inc. "The SPRIworks Fragment Library System Simplifying Next-Generation Sequencing Workflows", (2010), www.beckmancoulter.com/wsrportal/bibliography?docname=DS-14103.pdf.
Devonshire, A., et al., "Application of Next-Generation qPCR and Sequencing Platforms to mRNA Biomarker Analysis", Methods, Jan. 2013, vol. 59, No. 1, pp. 89-100.
European Patent Office, European Examination Report for EP3307907 dated Jan. 17, 2019.
European Patent Office, European Office Action for application 16732490, dated Sep. 26, 2019.
International Searching Authority, International Search Report and Written Opinion for PCT/EP2016/067149 dated Oct. 17, 2016.
International Searching Authority, International Search Report and Written Opinion for PCT/EP2016/063150 dated Sep. 13, 2016.
Janku, F., et al. "BRAF mutation testing with a rapid, fully integrated molecular diagnostics system." Oncotarget 6.29 (2015): 26886.
Japan Patent Office, Office Action for application 2017-563581, dated Aug. 6, 2019, with English Translation.
Soya, Y. Development of Molecular Testing Using Novel Gene Analyzer, Genecube System. Biological sample analysis, 2013, vol. 36, No. 4, p. 310-315. English Abstract.

* cited by examiner

OPTIMIZED CLINICAL SAMPLE SEQUENCING

OPTIMIZED CLINICAL SAMPLE SEQUENCING

CROSS-REFERENCE TO RELATED PATENT APPLICATIONS

The present application is a U.S. National Phase application of International Application No. PCT/EP2016/067148, filed on Jul. 19, 2016, which application claims the benefit of priority to European Patent Application No. 15178159.8, filed on Jul. 23, 2015, the contents of which are incorporated herein by reference in their entireties.

TECHNICAL FIELD

The present invention generally relates to automated systems capable of concomitantly performing quantitative PCR (qPCR) analysis of nucleic acids present in a biological sample, together with preparation of a sequencing-ready nucleic acid library from said sample, either simultaneously or sequentially. In a further aspect, the present invention also concerns automated methods for performing qPCR on a nucleic acid present in a biological sample together with simultaneous or sequential preparation of a sequencing-ready nucleic acid library from said sample.

BACKGROUND OF THE INVENTION

Quantitative polymerase chain reaction (qPCR), also known as real-time PCR, is a powerful and highly versatile tool for target nucleic acid analysis. Like many other PCR-based techniques, qPCR uses target-specific primers for amplification and/or detection of a nucleic acid of choice. Currently, qPCR is recognized as a diagnostic golden standard technique and is widely used in laboratories and clinics worldwide.

Among other fields and applications, qPCR is broadly employed in clinical oncology to discriminate between wild-type and mutant nucleic acids for both diagnostic purposes as well as to identify actionable alleles suitable for targeted therapies. The technique is rapid, robust, and works great in majority of those cancers that are known to be most likely driven by a limited number of well-defined mutations; for example, melanoma where mutated BRAF and NRAS are the usual suspects. However, in cases where the detection of the most likely expected mutation or a set of mutations fails, one may face a situation where a huge amount of genes would have to be analyzed (each with a different set of specific primers and/or probes) before at least one potentially actionable target is identified.

In such instances, it may become necessary to perform a diagnostic follow-up of a given cancer sample with a technique that provides a broader and sequence-independent gene coverage. A particularly suitable for this purpose approach involves high-throughput sequencing, also known as second generation- or next generation-sequencing (NGS), which stands in contrast to much slower classical Sanger strategy-based sequencing. Despite the ever-decreasing costs of NGS analyses (record low price of $1000 per genome reached in 2014), the technique still remains relatively costly. Furthermore, it is largely considered labor-intensive due to multiple preparatory steps such as verification of nucleic acid quantity and quality, followed by generation of a sequencing ready nucleic-acid library. Most importantly however, NGS produces large quantities of data per run which poses additional computational challenges for analyzing it and requires highly skilled personnel for data interpretation. Therefore, whenever possible, the much more economical and faster qPCR is the diagnostic approach of preference; nonetheless, NGS remains a valid and often valuable if not necessary follow-up option.

As mentioned above, a key consideration for a successful NGS analysis is whether the nucleic acid provided in a sample is present at a sufficient quantity and if it is of a sufficient quality for generating a satisfactory library for sequencing. Conventional nucleic acid verification methods used for this purpose involve standard approaches such as absorbance (optical density) measurement, agarose gel electrophoresis, or fluorometry e.g. using fluorescent DNA-binding dyes. More recently, in order to spare as much as possible from the nucleic acid sample intended for NGS, only a part of it is subjected to a PCR which product is then used for performing the necessary quantity and quality assessments. Commonly used for this purpose PCR products are generated e.g. using short interspersed nuclear elements (SINEs), like the Alu repeats, or long interspersed nuclear elements (LINEs) (cf. Buehler et al. 2010).

It should be noted that the above-listed preparatory steps exist as stand-alone assays which are performed only after a decision to proceed to NGS analysis has been taken. It is not a common practice to prepare a sequencing library prophylactically in order to secure nucleic acids obtained from a clinical sample in case an NGS follow-up would be required in some future. This is mainly because the quality control and library preparation steps take additional time from skilled personnel, thereby increasing the overall cost of the entire sample handling process. In fact, reagents' cost-wise, these steps are likely the cheapest part of the entire NGS workflow.

By automatically generating a sequencing-ready library already at the stage of the initial standard qPCR screening of clinical samples, one would not only save time and trained human resources but would also ensure better management of precious and limited in amount clinical samples. A further advantage of such solution would be the ability to immediately generate or use the information from the real-time-monitored qPCR reaction as an indication of nucleic acid quantity and quality, and thus its suitability for NGS library generation. The following advantage would be the ability to directly compare the qPCR results and the results later obtained from an NGS analysis of the library concomitantly generated with and on the same machine as said qPCR, either at the same time of (i.e. simultaneously) or just shortly after (i.e. sequentially), and, importantly, using the same pool of identically processed nucleic acid. Furthermore, by thus removing the usual temporal separation between a qPCR analysis and stabilization of the free nucleic acids in a form of a library, one could further minimize any potential analytical dichotomies between qPCR and NGS results, stemming from prolonged storage periods of biological samples or free nucleic acids isolated therefrom, which can cause their at least partial degradation.

The present invention addresses the above advantages by providing automated systems and methods for preforming a highly sensitive qPCR analysis combined with NGS library preparation from the same biological sample. By doing so, the present invention not only allows verification of sample quality together with preparing an NGS library but further provides means for immediate high-depth discovery of driver mutations in advance of NGS-provided broader insight to genomic alterations present in a given sample. This and other advantages of the present invention are presented in continuation.

SUMMARY OF THE INVENTION

The present invention is defined in the appended independent claims. Preferred embodiments are defined in the dependent claims. In particular, the present invention concerns an automated system for quantitative PCR (qPCR) analysis of a nucleic acid present in a nucleic acid source, such as a biological sample, received into said system and for concomitant preparation of a sequencing nucleic acid library from said nucleic acid source, the system comprising:
- a means for performing quantitative PCR (qPCR) comprising a thermocycling compartment comprising reagents necessary for performing a qPCR, further referred to as "thermocycling qPCR compartment";
- said system characterized in
- further comprising a means for preparing a nucleic acid library comprising a library compartment separate from the thermocycling qPCR compartment, said library compartment comprising reagents necessary for preparing a nucleic acid library including NGS-specific adapter sequences.

Preferably, the automated system of the present invention is a cartridge-based microfluidic system. Thus, in a further aspect, the invention provides a removable cartridge for the automated system according to the invention, said cartridge comprising:
- at least one thermocycling qPCR compartment comprising reagents necessary for performing a qPCR; and
- at least one library compartment separate from the thermocycling qPCR compartment, said library compartment comprising reagents necessary for preparing a nucleic acid library including NGS-specific adapter sequences.

In preferred embodiments, the cartridge of the invention further preferably incorporates means for receiving a biological sample and means for liberating nucleic acid from the biological sample Finally, the invention also provides method of performing qPCR with a concomitant preparation of a nucleic acid library on the automated system according to the invention, said method comprising the steps of:
- a) receiving a source of nucleic acid into the automated system, said source of nucleic acid comprising nucleic acid;
- b) optionally, liberating in said automated system the nucleic acid from at least a part of said received source of nucleic acid;
- c) performing qPCR on the nucleic acid provided in or liberated from the source of nucleic acid, the qPCR comprising thermocycling said nucleic acid in the thermocycling qPCR compartment comprised in said system;
- d) preparing a nucleic acid library in the library compartment comprised in said system;

wherein in that the steps c) and d) are performed on said automated system either sequentially or simultaneously.

Definitions

The term "quantitative PCR" or simply "qPCR" is herein given the definition of a laboratory technique based on the polymerase chain reaction (PCR), which is used to amplify and simultaneously detect or quantify a targeted DNA molecule. In contrast to standard PCR where the product of the reaction is detected at its end, i.e. after thermocycling has finished, the key feature of qPCR is that the DNA product is being detected during thermocycling as the reaction progresses in "real time"; hence, the alternative name of qPCR "real-time PCR". There currently exist many different types of qPCRs. For example, when starting with a reverse transcription (RT) step, qPCR can be used to quantify numbers of messenger RNAs and is then called a reverse transcriptase qPCR or an RT-qPCR. As used herein the terms "quantitative PCR" or simply "qPCR" will be employed with preference over the term "real-time PCR" or "RT-PCR" in order to avoid confusion with reverse transcription PCR, also frequently abbreviated as RT-PCR. Most qPCRs use one of the two most common methods for detecting the product amplification in real-time: (a) intercalation of non-specific fluorescent dyes with any double-stranded DNA, or (2) sequence-specific DNA probes consisting of oligonucleotides that are labelled with a fluorescent reporter which permits detection only after hybridization of the probe with its complementary target sequence. The fluorescent signals generated during thermocycling are detected by an appropriate optical detection system and tracked from the moment they pass the background threshold till the reaction reaches plateau. The copy number of the target sequences can be estimated using either relative or absolute quantification strategy, typically by analyzing the shape of the obtained amplification curve (standard curve strategy) or by determining when the signal rises above some threshold value (often called the Ct value, but soe times also Cp value or Cq value). In relative quantification, the target nucleic acid levels estimated in a given sample using the Ct or standard curve analysis are expressed as relative to values obtained for the same target in another reference sample, for example, an untreated control sample. Conversely, in absolute quantification the qPCR signal is related to input copy number using a standard curve or can also be calculated according to a more recent digital PCR method. For the moment being, the first strategy is still more prevalent and bases the estimation of the target DNA amount by comparing the obtained values with a previously made standard curve. These and other qPCR quantification strategies are broadly known in the art and their calculation can differ in smaller or greater depending on a given application and a qPCR system.

As used herein, the term "means for performing quantitative PCR" shall be understood as minimum necessary arrangement of reagents and elements for performing a qPCR. They will usually include any reagents allowing detectable in real time PCR thermocycling of a nucleic acid template received from a source of nucleic acid. Such reagents include but depending on the type of qPCR are not limited to a PCR-grade polymerase, at least one primer set, a detectable dye or a probe, dNTPs, PCR buffer etc. Further, the "means for performing quantitative PCR" will usually also include any standard known in the art minimal assembly of parts, which usually includes but is not limited to the following: (1) a suitable compartment (further referred to as a "a thermocycling qPCR compartment") where the real time-detectable thermocycling can take place. Such compartments can e.g. be formed by a chamber suitable for amplifying nucleic acids, i.e. made from appropriate material and providing for sufficient internal temperature regulation, and also comprising at least one wall allowing real-time detection of signals generated during such amplification, e.g. a wall transparent to light. Further, (2) means for varying temperature in this chamber or other compartment, as broadly known from various existing thermocycling machines. Then, (3) means for detecting the signals generated during the qPCR thermocycling, like an optical detector coupled to a computer etc. In brief, such minimal assembly will normally include any known in the art system or systems capable of initiating and maintaining the thermocycling reaction in the thermocycling qPCR compartment, adjusting and regulating the temperature to ensure stable thermocycling conditions therein etc.; further, it will also include any appropriate detection device or devices, means for data processing (e.g. a computer alternatively connected to a database), and output systems allowing to read and monitor the thermocycling of the qPCR reaction in real-time (usu. a computer screen displaying the reaction progress in an appropriate graphic user interface); as well as any software packages suitable for operating the machinery and/or displaying and possibly also aiding the interpretation of the obtained results.

Further, as used herein, the term "sequencing library" or "sequencing nucleic acid library" refers to a set of polynucleotides, most often of DNA type, that are ready for sequence analysis, in particular using any of the currently known next-generation sequencing (NGS) strategies. In line with this, in a currently preferred embodiment of the invention, a sequencing library is composed of a plurality of PCR-amplified DNA molecules, most preferably fused with adapter molecules (or adapter sequences) compatible with a given NGS strategy of choice. A comprehensive overview of sequencing library types and ways of preparing them can be found in a review of van Dijk et al. *Exp Cell Res.* 2014.

Similarly, as used herein, the term "means for preparing a nucleic acid library" shall be understood as minimum necessary elements for preparing an NGS-suitable nucleic acid library, which include at least a compartment where a nucleic acid received from a source of nucleic acid can be subjected to nucleic acid library preparation; the minimum necessary reagents for the library preparation such as appropriate enzyme or a mix of enzymes, NGS-strategy-specific adapter sequences or adapters, buffer etc.); and also a standard known in the art machinery and software suitable for of e.g. initiating and/or directing the library preparation procedure. As used herein the term "reagents necessary for preparing a nucleic acid library" is to be understood as any mix of reagents known in the art that are sufficient for preparing a nucleic library that can be used for NGS. Preferably, "reagents necessary for preparing a nucleic acid library" can to be construed as any mix of reagents known in the art that are sufficient for preparing a nucleic library that can be directly used for NGS, i.e. comprising NGS-specific adapter sequences that are compatible with a given NGS strategy of choice. Such reagents may comprise primer sequences wherein the NGS-specific adapter sequences are included in the sequences of primers and the reagent mix comprises enzymes, substrates, and buffering conditions which allow to perform a library PCR with such primers. Alternatively, such NGS-specific adapter sequences can be suitable for ligation and can be provided in a reagent mix also comprising enzyme ligase.

Further, the term "means for liberating or purifying nucleic acid from the biological sample" is to be understood as any plurality or chemical reagents and/or physical elements as known in the art that are known to be used for liberating nucleic acids from cells or other structures in a biological sample, and, in case of purification, sufficiently separating said nucleic acids from unwanted sample debris into an acceptably pure form (wherein the term "acceptably" depends on the further purpose of such purified nucleic acids), usually in an aqueous solution. Chemical reagents suitable for such purpose include e.g. any known in the art detergents and/or buffers comprising detergents, chaotropic agents, nuclease inhibitors etc. that are used in tissue or cell disrupting and/or liquefying, and thus releasing nucleic acids contained therein into solution. Similarly, physical elements known in the art to be used in various methods of sample processing for the purpose of nucleic acid liberation/purification include e.g. silica solid supports such as resins in spin columns, silica membranes, beads etc.; further mechanical disruptors or machines generating disruptive energy such as sonicators etc.

Then, the term "nucleic acid" and its equivalent "polynucleotide", as used herein, refer to a polymer of ribonucleosides or deoxyribonucleosides comprising phosphodiester linkages between nucleotide subunits. Nucleic acids include but are not limited to DNA and RNA, e.g. including genomic DNA, mitochondrial or meDNA, cDNA, mRNA, rRNA, tRNA, hnRNA, microRNA, lncRNA, and various modified versions thereof. Nucleic acids can most commonly be obtained from natural sources like biological samples obtained from different types of organisms. On the other hand, nucleic acids can also be synthesized, recombined, or otherwise produced in any of the known human-devised methods (e.g. nucleic acid amplification method like PCR).

As used herein, the term "source of a nucleic acid" is to be understood as any substance whether liquid or solid, comprising or expected to comprise nucleic acid. A source of nucleic acid can e.g. be an artificially created solution comprising a synthetic or recombinant nucleic acid such as among many other a solution containing a ligation product, an electrophoresis marker (so called "ladder"), a primer stock etc. Most commonly however, a source of nucleic acid will be a biological sample obtained from an organism or cells forming or derived thereof, preferably a clinical sample obtained from a patient.

As used herein, the term "biological sample", or simply "sample", is intended to include a variety of biological sources that contain nucleic acid and/or cellular material, for example including: cultures of cells such as mammalian cells but also of eukaryotic microorganisms, body fluids, body fluid precipitates, lavage specimen, fine needle aspirates, biopsy samples, tissue samples, cancer cells, other types of cells obtained from a patient, cells from a tissue or in vitro cultured cells from an individual being tested and/or treated for disease or infection, or forensic samples. Non-limiting examples of body fluid samples include whole blood, bone marrow, cerebrospinal fluid (CSF), peritoneal fluid, pleural fluid, lymph fluid, serum, plasma, urine, chyle, stool, ejaculate, sputum, nipple aspirate, saliva, swabs specimen, wash or lavage fluid and/or brush specimens.

Once a biological sample is provided into the systems or during performing the methods of the invention, it will usually be contacted with a composition to provide a lysate in which nucleic acid is released. As used herein, by "contacting" is meant bringing together, exposing, incubating, or mixing of the sample and the composition. "Releasing" refers to liberating, obtaining and/or reversal of cross-linking. For liberating nucleic acid from a sample, protease activity and pH-buffering may be required from the composition. Releasing may require from the composition potential precipitating activity of components other than nucleic acid present in the investigated sample and removal/dissolving of fixative. Releasing may require conditions such as heating or High-Intensity Focused Ultrasound (HIFU). In one embodiment in accordance with the spirit of the invention, a biological sample is introduced into a cartridge compatible with an automated system such as a diagnostic analyzer, wherein the sample processing steps involving contacting with various solutions and releasing of nucleic acids take place.

Further, the term "cartridge" is to be understood as a self-contained assembly of chambers and/or channels, which is formed as a single object that can be transferred or moved as one fitting inside or outside of a larger instrument suitable for accepting or connecting to such cartridge. Some parts contained in the cartridge may be firmly connected whereas others may be flexibly connected and movable with respect to other components of the cartridge. Analogously, as used herein the term "fluidic cartridge" shall be understood as a cartridge including at least one chamber or channel suitable for treating, processing, discharging, or analyzing a fluid, preferably a liquid. An example of such cartridge is given in WO2007004103. Advantageously, a fluidic cartridge can be a microfluidic cartridge. In the context of fluidic cartridges the terms "downstream" and "upstream" can be defined as relating to the direction in which fluids flow in such cartridge. Namely, a section of a fluidic path in a cartridge from which a fluid flows towards a second section in the same cartridge is to be interpreted as positioned upstream of the latter. Analogously, the section to which a fluid arrives later is positioned downstream with respect to a section which said fluid passed earlier.

In general, as used herein the terms "fluidic" or sometimes "microfluidic" refers to systems and arrangements dealing with the behavior, control, and manipulation of fluids that are geometrically constrained to a small, typically sub-millimeter-scale in at least one or two dimensions (e.g. width and height or a channel). Such small-volume fluids are moved, mixed, separated or otherwise processed at micro scale requiring small size and low energy consumption. Microfluidic systems include structures such as micro pneumatic systems (pressure sources, liquid pumps, micro valves, etc.) and microfluidic structures for the handling of micro, nano- and picoliter volumes (microfluidic channels, etc.). Exemplary microfluidic systems have been described in EP1896180, EP1904234, and EP2419705 and can accordingly be incorporated applied in certain embodiments of the presented herein invention.

BRIEF DESCRIPTION OF FIGURES

For a fuller understanding of the nature of the present invention, reference is made to the following detailed description taken in conjunction with the accompanying drawings in which.

DETAILED DESCRIPTION OF THE INVENTION

Figure 1:
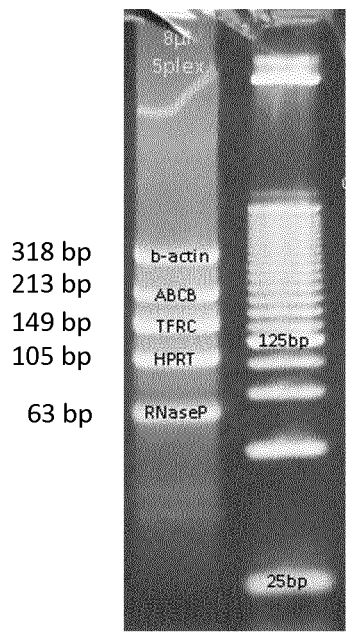
FIG. 1: shows 5 DNA bands on an electrophoretic gel, corresponding to 5 products of a 5plex qPCR performed on a liquefied FFPE sample.

The present invention generally integrates qPCR-based systems and methods for assessment of nucleic acid samples together with systems and methods for preparation of NGS libraries. Such integration provides for a faster and more efficient diagnostic workflow and is particularly advantageous for using the information about nucleic acid quality as inferred from a qPCR run, directly for deciding whether said nucleic acid is of sufficiently suitable for proceeding with an NGS data analysis In line with this, because exactly the same and identically-processed nucleic acid is used for both qPCR and library preparation, the present invention also provides a unique means for directly comparing the diagnostic information on key target mutations as screened by qPCR with a broader genetic landscape as obtained from the NGS data.

In particular, the present invention provides an automated system for quantitative PCR (qPCR) analysis of a nucleic acid present in a nucleic acid source (e.g. a biological sample) received into said system and for concomitant preparation of a sequencing nucleic acid library from said nucleic acid source, the system comprising:

a means for performing quantitative PCR (qPCR) comprising a thermocycling qPCR compartment suitable for amplifying nucleic acids and allowing detection of signals generated during such amplification, said thermocycling qPCR compartment comprising reagents necessary for performing a qPCR;

said system characterized in further comprising a means for preparing a nucleic acid library comprising a library compartment separate from the thermocycling qPCR compartment, said library compartment comprising reagents for preparing a nucleic acid library.

Preferably, the qPCR performed in the thermocycling qPCR compartment is a multiplex qPCR, i.e. a qPCR simultaneously amplifying and detecting multiple sequences in a single reaction. A multiplex qPCR uses multiple primer sets in a single qPCR mixture and thus generates multiple products in one tube, chamber, or other type of a qPCR thermocycling compartment. Multiplex qPCR using two primer sets (usually pairs) is called a duplex, often denoted 2plex. Similarly, a multiplex qPCR with three primer sets is a triplex or a 3plex. Preferred in the present invention multiplex qPCR arrangements include a 2plex, a 3plex, a 4plex, a 5plex, a 6plex, a 7plex, or more.

Therefore, in a preferred embodiment, the reagents necessary for performing a qPCR comprise a plurality of primer sets, each directed to a different amplicon, wherein said plurality is preferably 2, 3, 4, 5, 6, 7, or more.

It is well known in the art that designing a robust multiplex qPCR is not easy as the assay requires that the multiplicity of individual primer sets (usually primer pairs) will specifically target their unique amplicons in one reaction tube and thus under a single set of reaction conditions. Primer design will typically take into account primer purity (17 to 30 bases in length); balance G/C and A/T-rich domains (20 to 70% G+C); set melting temperature between 55-80° C.; avoid creating complementary 3'end base pairs; avoid primer self-complementary; and avoid 1 or more C's or G's at the 3' end of primers, especially when the multiplex is to be performed on complex samples such as eukaryotic genomic DNA. Several web-based primer design software tools are available that help design PCR primers (e.g. Primer3Plus). Other factors, such as the relative concentration of the primers, the right concentration of the PCR buffer components, balance between the magnesium chloride and deoxynucleotide concentrations, cycling temperatures, and DNA thermocycling polymerase etc. also often have to be fine-tuned for a successful multiplex qPCR. Notably, finding an optimal combination of the annealing temperature and buffer concentration is essential in multiplex PCR to obtain highly specific amplification products. Magnesium chloride concentration needs to be proportional to the amount of dNTP, while primer concentration for each target should be relatively robust. A choice of a proper polymerase can also have impact on the outcome of the reaction. In theory, multiplex PCR can be performed with standard PCR polymerase; however in practice it is preferred that highly processive and sensitive DNA polymerases such as GOTAQ® or AMPLITAQ™ are used. For particularly sensitive applications, further modifications of multiplex qPCR such as the ones using DNAzymes or MNAzymes may be advantageous for the application in the present invention. The list of the mentioned-herein factors and multiplex optimization strategies is by no means to be interpreted as extensive, which will be immediately appreciated by any person skilled in the art.

In preferred embodiments of the invention, the quantification of the qPCR in the systems and methods of the invention is based on the standard curve method; however, other quantification strategies can also be used, as will be immediately appreciated by any skilled person.

Similarly, many different general types of fluorescent dyes or detection probes can be used in the systems and methods of the present invention. In preferred embodiments sequence specific probes will be used, e.g. selected from exonuclease probes, hybridization probes, or molecular beacons. Such probes not only add specificity to the assay, but are also key for enabling multiplex applications. As shown in the examples, the methods of the invention were successfully applied with the use of TAQMAN® probes but other probes would be suitable as well.

In a further aspect of the present invention, it has been observed that a multiplex qPCR that is particularly suitable for assessing nucleic acid quality is a multiplex qPCR generating amplicons varying in sizes. The size range of the amplicons varies from a smaller size Ax to a higher size Ay (with x<y), typically in the size range of 50-600 bp. Preferably the smaller Ax size ranges from 50 to 110 bp and can be of any length in between that range. Preferably Ax is between 60 bp+/−10 bp. As shown further herein in Examples, Ax is 63 bp or 105 bp. Preferably the larger Ay size ranges from 300 to 550 bp and can be any length in between that range. As shown in further in the Examples, Ay is 504 bp (e.g. for the TRFC gene) or alternatively 318 bp (e.g. for the beta-actin gene). In case of RNA sequencing, particularly in applications focusing on microRNA (e.g. 15-35 bp size range), the smaller Ax size range may need to be lowered accordingly. As will be appreciated by any skilled artisan, during the multiplex qPCR design for the purposes of the present invention, the preferred amplicon sizes may advantageously be selected in accordance with the NGS application of choice in order to provide the most adequate estimation about the NGS coverage according to amplicon length.

In principle, for performing such quality control multiplex qPCR, targets can be selected from any genes or genomic regions. For diagnosis of genetically unstable conditions like cancer, it is better however, to avoid disease-sensitive regions that are likely to have their sequence mutated or change in copy number. Therefore, in a preferred embodiment, the targets of the quality control multiplex qPCR are selected from intra-exon sequences of single copy genes, such as a housekeeping gene. A further advantage of said solution is that the same target sequences directed to intra-exon regions can be used in assessment of both DNA as well as in RNA quality as a library material. Because of the latter, such design of the quality control multiplex qPCR multiplex of the present invention is particularly useful when it is desired to sequence both the genome and the transcriptome from one sample, which requires construction of and thus also quality verification for both DNA- and RNA-based. Thus, in one preferred embodiment, the quality control multiplex qPCR to be used in systems and method of the invention, targets at least one intra-exon sequence in a single copy gene. Possibly, one, two, three, four, five, six, seven or more intra exon sequence in a one, two, three, four, five, six, seven or more single copy genes are targeted. Alternatively to housekeeping genes, in DNA library construction, repetitive sequences (e.g. LINEs, or SINEs such as Alu elements) may be the targets of interest. As a non-limiting example shown in the example section, the methods of the invention are successfully practiced on intra-exon sequences of the RNaseP, HPRT1, Beta-Actin, TRFC and ABCB1 genes.

In a preferred embodiment, the automated system according to the invention further comprises at least one nucleic acid source-receiving compartment, positioned upstream with respect of the thermocycling qPCR compartment and of the library compartment, into which a user can easily provide (e.g. insert or pour) a nucleic acid-congaing source such as a biological sample they wish to screen.

In preferred embodiments, the nucleic acid source is a biological sample. Preferably, the sample is a fresh sample, a fresh frozen sample, a fine needle aspirate, a sample that has been treated for preservation and may contain cross-linking of reactive sites due to fixation treatment, a wax-contacted or wax-embedded sample, an FFPE sample in the form of an FFPE slice, a liquid sample such as a urine sample, a blood sample, a serum sample, or any other clinical sample.

In another embodiment highly compatible with the above embodiment, the automated system of the invention also comprises a means for liberating or purifying nucleic acid from the received nucleic acid source, said means positioned upstream with respect of the thermocycling qPCR compartment and of the library compartment and downstream with respect to and being in fluid communication with the nucleic acid source-receiving compartment or alternatively comprised in said nucleic acid source-receiving compartment. Such means may comprise any complex or simple arrangement of elements that perform functions leading to nucleic acid separation and/or purification from the remaining components of the received sample.

Once introduced to systems and methods of the invention, a biological sample will usually be processed by contacting it with a composition that provides for releasing of nucleic acids. In preferred embodiments, the composition is optimized for use in microfluidic analyzers and preferably contains surfactants rather than organic solvents. Mixing with said composition usually also facilitates transporting of such processed sample through a microfluidic system. In embodiments wherein the sample is an FFPE sample, the surfactant comprised in said composition will preferably be non-ionic. Nucleic acids obtained from FFPE samples typically contain nucleotide-to-nucleotide and nucleotide-to-protein cross-links, base modifications and other chemical modifications that affect the integrity of the nucleic acid. Preferred methods of the present invention incorporate a non-ionic surfactant and permit automated removal of embedded wax and liberation of the components without use of organic solvents. This is particularly beneficial because it puts the liberated nucleic acids in a condition and environment that interfaces with downscale applications requiring enzymatic activity such as nucleic acid amplification via PCR. In one embodiment, the lysate and/or components released from the sample will be further processed in diagnostic analyzers using microfluidic systems.

Optionally, the liberated nucleic acid is provided in a form sufficiently pure for being directly used as a template for a qPCR and a nucleic acid library construction on the automated system of the invention. In a preferred embodiment, the nucleic acid-liberating means performs its function in a fluidic or microfluidic arrangement. In such instance, the elements forming such nucleic acid-liberating means may comprise a series of consecutive or otherwise fluidly interconnected compartments, like chambers or channels, at least some of which being supplied with reagents like lysis buffers, enzyme solutions, extraction buffers, binding buffers and/or wash buffers; or optionally comprising any of the known in the art physical barriers, such as filters or high-affinity resins, that facilitate processes like mechanical sample clearing or nucleic acid binding, washing, and releasing. Such and alternative means for liberating nucleic acids are well known in the art and therefore will not be discussed herein in greater detail.

In another advantageous embodiment, the automated system further comprises means for dividing the received nucleic acid source, or the nucleic acid liberated or purified from said source, between at least the thermocycling qPCR compartment and the library compartment. Such means could e.g. comprise two separate channels extending from the nucleic acid source-receiving compartment or the compartment whereto the liberated from said source nucleic acid is deposited in the last step of the nucleic acid liberation process, into the thermocycling qPCR compartment and into the library compartment, respectively. In order to actively transport the nucleic acid between the compartments of choice, the automated system of the invention could provide a pressure gradient capable of pushing or pulling a desired amount of fluid into prescribed direction. Generation of such pressure gradients by means of pumps, suction devices, manifolds etc. is widely employed in contemporary microfluidic systems and thus well known in the art.

In another prefer embodiment, the automated system of the invention comprises more than one thermocycling qPCR compartment each being physically separate from the library compartment, wherein each of the thermocycling qPCR compartments comprises reagents necessary for performing a qPCR and is suitable for amplifying nucleic acids and allowing detection of signals generated during such amplification. In such embodiment, the second and consequent thermocycling qPCR compartment can preferably be used for screening specific markers of choice.

The present invention preferably provides cartridge-based systems. Therefore, in another aspect, an automated system is provided wherein the one or more thermocycling qPCR compartments and the library compartment, preferably also the nucleic acid source-receiving compartment and the means for liberating nucleic acid from the received nucleic acid source, are comprised in a cartridge engageable with said automated system, preferably being a fluidic or microfluidic cartridge.

Microfluidic cartridges suitable for the purposes of the present invention are known in the art. Preferably, such cartridges may contain at least two reaction chambers comprising the thermocycling qPCR compartment and the library compartment, and one or more fluid chambers. Some of the fluid chambers may hold fluid which is used for producing lysate from the sample. Other chambers may hold fluids such as washing fluids and amplification solution. Separate reaction chambers are used as the thermocycling qPCR compartment and the library compartment. The chamber configured to serve as the thermocycling qPCR compartment comprises a number of primer sets, along with other amplification reagents and enzymes required for performing a qPCR. The other chamber configured to serve as the library compartment is adapted to performing the steps of constructing a nucleic acid library for an NGS application of choice. Parts of the sample will be transferred to the reaction chambers and to make such transfer possible, chambers are connected to one or more fluid channel. In at least one, but preferably each of these fluid channels a valve means may be provided, which valve means preferably normally closes the fluid channel, but opens the fluid channel upon actuation of the valve means therewith placing the respective two chambers in fluid communication. The valve means may be designed as a one-way valve.

In another advantageous embodiment, the present invention also provides an automated system, wherein the means for performing qPCR are adapted to, i.e. comprise all the components necessary to, perform any of the following:
  quality control (QC) qPCR suitable for assessing quality of nucleic acid subjected thereto; or
  non-quality multiplex qPCR suitable for determining the presence or amount of genomic alterations potentially present in the nucleic acid subjected thereto.

Further, an automated system is provided, wherein the QC qPCR is a multiplex QC qPCR and wherein the automated system further comprises a means for generating a quality metric output from the data obtained from said multiplex QC PCR. Such quality metric output may characterize either the nucleic acid to be used to make the library or the nucleic acid from the library itself after said library has already been made in the library compartment. Therefore, in possible embodiments, the automated system of the invention may further comprise means for transferring a part of the nucleic acid from the library made in the library compartment.

In a particularly preferred embodiment, the automated system of the invention is capable of operating the thermocycling qPCR compartment and the library compartment simultaneously or sequentially. This means that three modes of operation can be envisaged: (i) both compartments operate once nucleic acid is fed into them, thus library preparation is independent of and proceeds in parallel with qPCR; and (ii) first, qPCR is made, then library is made; like this the decision to prepare a library for sequencing is made once the results of the qPCR are known and may depend on these results; (iii) first, the library is made, then qPCR is performed on the library for the verification of the library quality.

The option (i) above describes the simultaneous operation in which the preparation of a library for NGS from a part of a nucleic acid sample is run simultaneously with a qPCR assay on another part of the same nucleic acid sample, and both are preferably performed in parallel in a cartridge-based microfluidic system. As used herein the term "simultaneously" or "in parallel" refers to happening or being done at the same time. In such arrangement, the qPCR is being performed on a part from a nucleic acid sample at the same time as the nucleic acid library for NGS application is being constructed from another part from the same nucleic acid sample. In other words, during the simultaneous operation, both the sample analysis via qPCR and library construction are executed by the automated system of the invention at the same time.

Conversely, the options (ii) and (iii) above can both be described as operating "sequentially". In one possible embodiment of the sequential operation at least two thermocycling qPCR compartments operate on the automated system of the invention. For example, first qPCR can be done to read the expression of interesting markers and verify the quality of nucleic acid source fed into the system. Following this first qPCR (sequentially), or to save time in parallel with said first qPCR (simultaneously), a library is constructed. Then, a second or control qPCR can be performed on the thus constructed library to verify whether its quality is sufficient for subjecting it to further applications, such as sequencing.

With regard to the sequencing library preparation or construction, currently there exist many different ways of generating a sequencing-ready library, and their choice naturally depends on which NGS strategy is intended to be performed. In general, NGS library generation involves generation of nucleic acid fragments, which are compatible with given NGS. Therefore, in a preferred embodiment, an automated system is provided wherein the library compartment comprises means of generating nucleic acid fragments from the nucleic acid received into said library compartment.

For most commercially available NGS platforms, amplification of nucleic acid fragments is necessary to generate sufficient copies of sequencing templates. Thus, preferably, the nucleic acid fragments are generated in a PCR, further referred to as "library PCR". Suitable library PCRs are known in the art and include methods such as bridge amplification or emulsion PCR.

Most frequently, nucleic acid fragments forming a sequencing-ready library contain NGS platform-specific oligonucleotide adapters. Such adapters can be incorporated in the nucleic acid fragments via ligation or via PCR. In a particular embodiment in accordance with the above, the library compartment comprises means for attaching oligonucleotide adapters to at least one, preferably both ends of the nucleic acid fragments. Advantageously, the nucleic acid fragments are generated in a library PCR and wherein attaching oligonucleotide adapters to said nucleic acid fragments is performed by including an adapter sequence in a sequence of at least one primer used in said library PCR.

The nucleic acid fragment-containing NGS libraries can be obtained from a nucleic acid source of interest, such as genomic DNA, double-stranded cDNA, and PCR amplicons. The presence of adapter sequences enables selective clonal amplification of the library molecules.

As already state above, nucleic acid library construction is needed for DNA sequencing, RNA sequencing, and other applications such as sequencing-based methylation analysis. RNA sequencing (RNA-seq) is a method of investigating the transcriptome of an organism using deep-sequencing techniques. Total RNA generally contains only a very small percentage of coding or functional RNA; ribosomal RNA (rRNA: up to 80-90% of the total RNA), and to a lesser degree transfer RNA (tRNA), make up the majority of the RNA in a sample. Often, in order not to use 80-90% of one's sequencing capacity on repetitive rRNA sequences, rRNA can be removed from the sample prior to sequencing. The RNA after removal of rRNA is made into a library. This involves creating double-stranded cDNA through reverse transcription from the RNA (or fragmented RNA). This double-stranded cDNA may then be handled as normal genomic DNA throughout the remaining library construction process, including linking it with appropriate NGS-strategy specific adapters.

In another aspect, an automated system is provided further comprising a recovery compartment for recovering any of the following:
 a part of the nucleic acid source received into the automated system;
 a part of the liberated nucleic acid liberated in the automated system;
 at least a part of the nucleic acid library prepared in the automated system Such recovery compartment may comprise or simply be made of another chamber wherein no reaction takes place during the operation of the system of the invention. Such recovery would preferably be easily accessible from outside the present automated system or a cartridge of the automated system. For example, it could comprise a wall made of a pierceable material (e.g. a foil or a film) that can be pierced by a needle of a syringe or a pipette, allowing aspiration of its contents. Alternatively, the recovery compartment could be selectively brought in fluid communication and filled in with any of the above by means on pumping and following instructions given by the user through an interface of the automated system of the invention.

In a possible embodiment, such recovery compartment could be an external container e.g. plastic tube or a vial, engageable with or connectable to the automated system of the invention. In such instance, any of the compartments as follows:
 the compartment housing at least a part of the nucleic acid source received into the automated system or at least a part of the nucleic acid liberated from said source;
 the library compartment;
 thermocycling qPCR compartment;
could comprise a structure (e.g. an extension like a channel or an zone engageable with an element forming a channel) capable of brining it in fluid communication with the recovery compartment by any means capable of transporting at least a part of the content comprised in any one of said above-listed compartments into the recovery compartments.

In an advantageous embodiment, the library compartment can comprise a structure capable of brining it in fluid communication directly with a compartment where NGS is performed, possibly wherein said compartment is comprised in another system a system such as an automatic sequencer.

In a further aspect the present invention also provides an advantageous method of performing a qPCR analysis with a concomitant library preparation. In a conventional approach, nucleic acid samples are first subjected to quality control steps and only after the results of these steps are known, said samples are then used for the generation of sequencing library. In such consecutive processing, nucleic acid are stored for a certain amount of time before the results are known, during which period they can be subject to degradation. Thus, despite being characterized as suitable for library preparation in the earlier quality control assay, a nucleic acid sample by the time it is used for library construction can already be of decreased quality following e.g. too many thaw-freezing cycles or other mistakes during storage. In some cases, particularly applicable to RNA, this may even lead to NGS failure. Also, a consecutive approach is laborious, time-consuming, and comes with a risk of mixing data from different samples. The present invention solves the above-mentioned problems by providing a method that comprises the step of running a quality control qPCR concomitantly with the step of constructing of an NGS-suitable library using the same nucleic acid sample on the same automated system. Preferably, both of these steps are performed in one cartridge that fits in a cartridge-based microfluidic system.

Therefore, the present invention provides a method for performing qPCR with a concomitant preparation of a nucleic acid library on the automated system according to the invention, wherein said system comprises at least one thermocycling qPCR compartment and a library compartment separate from said at least one thermocycling qPCR compartment, said method comprising the steps of:
  a) receiving a source of nucleic acid into the automated system, said source of nucleic acid comprising nucleic acid;
  b) liberating or purifying in said automated system the nucleic acid from at least a part of said received source of nucleic acid;
  c) performing qPCR on the nucleic acid liberated or purified from the source of nucleic acid, said qPCR comprising thermocycling said nucleic acid in a thermocycling qPCR compartment comprised in said system and suitable for amplifying nucleic acids and allowing detection of signals generated during such amplification;
  d) preparing a nucleic acid library in the library compartment comprised in said system; wherein in that the steps c) and d) are performed on said automated system either sequentially or simultaneously.

Preferably, a method is provided wherein the steps c) and d) are performed on said automated system on a removable cartridge. Most preferably, a method is provided wherein the steps a) to d) are performed on said automated system on a cartridge.

In a preferred embodiment of the method of the invention, the step d) comprises a step of performing PCR, further referred to as "library PCR".

As explained above, one of the aspects of the invention involves running the control qPCR concomitantly with the preparation of a library for NGS, wherein both of the procedures use nucleic acid from the same source (sample), preferably being nucleic acid liberated from a clinical sample. In a preferred embodiment, both of the procedures are performed in one cartridge, preferably being a microfluidic cartridge engageable with an analyzer-type apparatus so that the cartridge is a self-contained disposable platform for performing the steps of the method according to the present invention. In such advantageous embodiment, all of the reagents required for performing the method of the invention are pre-positioned within such cartridge, for storage considerations preferably in a dried-down or a lyophilized form.

Therefore, in another preferred embodiment, the present invention also provides a cartridge for the automated system according to the invention, wherein said cartridge comprises:
  at least one thermocycling qPCR compartment comprising reagents necessary for performing a qPCR; and
  at least one library compartment separate from the thermocycling qPCR compartment, said library compartment comprising reagents necessary for preparing a nucleic acid library.

In a preferred embodiment, such cartridge would also further comprise
  at least one nucleic acid source-receiving compartment and preferably also means for liberating nucleic acid from the received nucleic acid source; and
  means for dividing the received nucleic acid source or the nucleic acid liberated from said source between at least the thermocycling qPCR compartment and the library compartment, and preferably also
  cartridge-specific identifier for automated cartridge or patient identification.

Preferably, such cartridge is integratable in a higher-throughput automation platform featuring integrated "sample-in, quality checked nucleic acid library-out" approach. Along these lines, nucleic acid quality metrics measured within the thermocycling qPCR compartment will be delivered along with the nucleic acid library for use in NGS. Based on the quality metric output, the nucleic acid library can be selected or deselected in an automated system of the invention for being subjected further to an NGS application.

The present invention provides for an effective automation of workflow with the different steps from sample-in to metrics-out. The presented herein approach has a great potential for providing a minimal turn-around times, lower costs and improved NGS success rates. The latter makes the automated systems, methods, and cartridges of the invention particularly suitable for the use with challenging samples such as FFPEs samples. The latter at least partially stems from the fact that the approach of the present invention minimizes variability observed between consecutive runs performed on the same sample following prolonged storage periods and thus allows to more correctly asses the nucleic acid condition prior to NGS library construction.

It is to be understood that both the foregoing general description and detailed description are only exemplary and explanatory and are not restrictive for the invention as claimed. In this application, the use of singular includes the plural unless specifically stated otherwise. In this application the use of "or" means "and/or" unless stated otherwise. The use of the terms "including", "includes" or "included" is not limiting.

EXAMPLES

Figure 2:
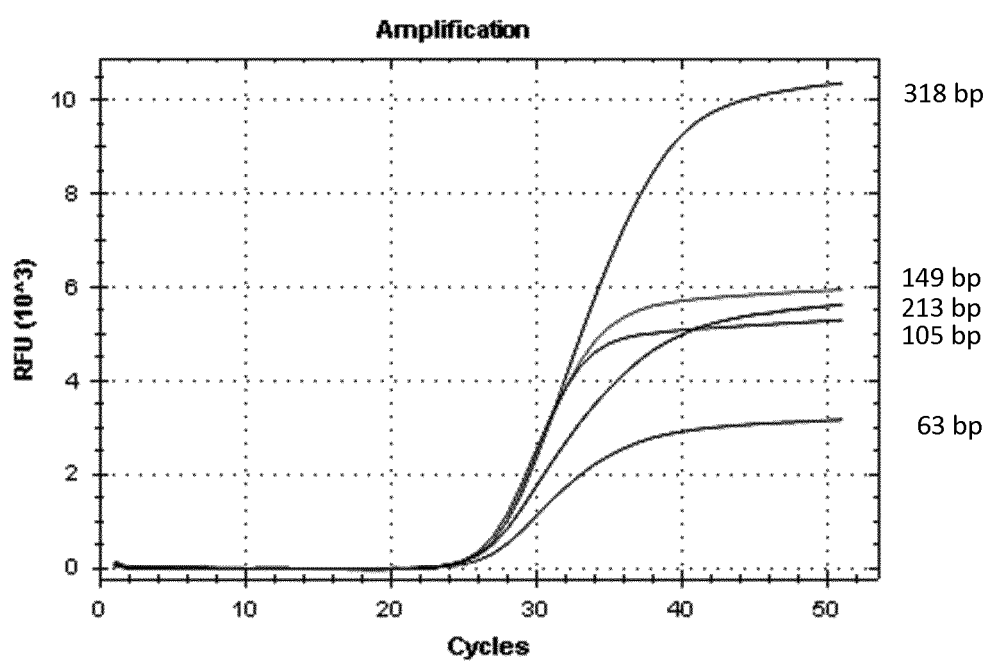
FIG. 2: shows qPCR amplification curves for the 5 products of the 5plex qPCR shown in FIG. 1.

Example 1: Development of a QC qPCR for an Automated Sample-to-Output Assessment of Nucleic Acids First, a quality control (QC) qPCR assay was developed for the purpose of assessing the amount and quality of nucleic acids present in a sample in a fully automated manner. The present QC qPCR tests for the presence of amplicons of various lengths, each derived from a different single copy human gene, and serves to assess nucleic acid suitability for NGS application. The amplicons and their lengths are as follows: (1) 63 bp fragment from human RNaseP gene; (2) 105 bp fragment from HPRT; (3) 149 bp fragment from TFRC; (4) 213 bp fragment from ABCB; and (5) 318 bp fragment from β-actin. The amplification of the fragments in one PCR reaction (5plex) was initially verified using a qPCR performed on a liquefied FFPE sample (Horizon FFPE sample) with a GOTAQ® polymerase and TAQMAN® probes (composition as specified by the supplier). The qPCR programme was 5' hold 95° C., followed by 50 cycles of 5" 95° C. 44" 64° C. FIG. 1 shows the obtained fragments (left lane) next to a DNA ladder (right lane) on a SYBR green stained 10% polyacrylamide gel following electrophoresis in TBE. The corresponding qPCR profile of the same sample shown in FIG. 2 (sizes of amplicons indicated next to the corresponding curves). The Cq values determined with the regression algorithm contained within the Biorad CFX Manager 3.1 are: (1) 26.1 for the 63 bp fragment (RNaseP); (2) 25.6 for the 105 bp fragment (HPRT); (3) 26.0 for the 149 bp fragment (TFRC); (4) 26.2 for the 213 bp fragment (ABCB); and (5) 27.4 for the 318 bp fragment (β-actin).

Figure 3:
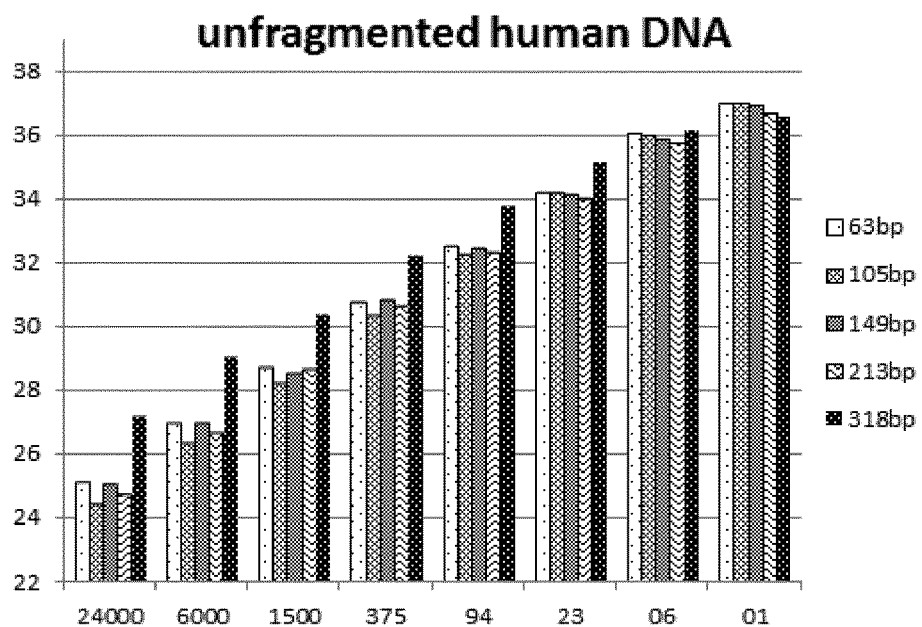
FIG. 3: shows a Cq to copy number histogram for at least 4 replicates of each of the 5plex qPCR products.
Figure 4:
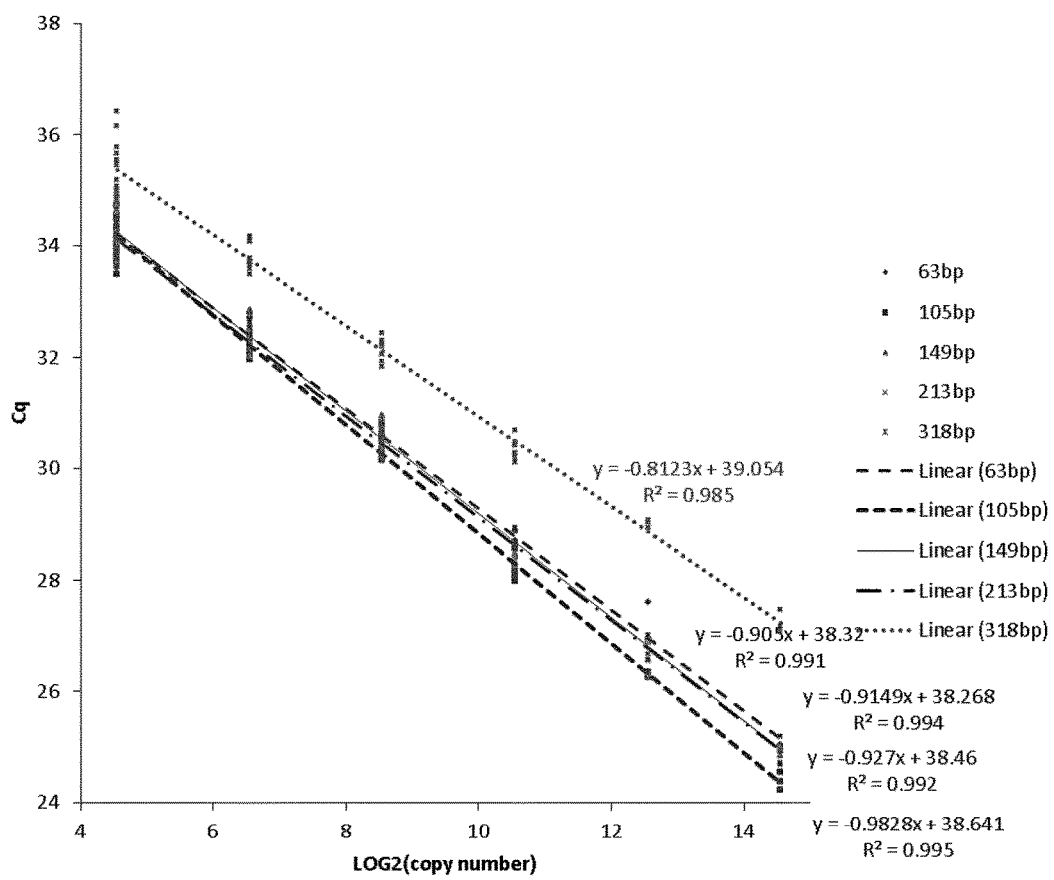
FIG. 4: shows R squared value determination for each of the 5plex qPCR products.

Next, the 5plex performance on unfragmented human genomic DNA was assessed to obtain standard curves with R squared values for each of the 5 amplicons. To do so, non-fragmented human genomic DNA at 173 μg/ml (Promega) was used as a substrate and the copy number was deduced using 3.3 pg/haploid genome as a premise. 4 replicates at 24000 copies per PCR, 4 replicates at 6000 copies, 8 replicates at 1500 copies, 8 replicates at 375 copies, 12 replicates at 94, 16 replicates at 23 copies, 20 replicates at 5.9 copies and 24 replicates at 1.5 copies per PCR were amplified and the Cqs determined as described above. The median Cq values were determined while omitting non-amplifications (so called flatliners). The histogram representing this experiment is shown in FIG. 3. The standard curves were deduced for each amplicon using logarithmic regression and the R squared value was determined as exemplified in FIG. 4 for the complete dataset and the dataset without the Cq values from both 5.9 and 1.5 copies per PCR, respectively. As expected, the R squared values approach 1 better with only data points in double digits copy number. For Cq values below 34, equations with the highest R squared values were used. Notably, for Cq values above 34, the quantification is known to be less accurate due to stochastic effects. The thus calculated according to said equations copy numbers of each of the 5 amplicons allow for the determination of both the useful DNA content and the degree of nucleic acid fragmentation in a given sample. An analysis of the direction coefficient of the linear regression between the log 2 (copy number input) and the Cq provides further indication of the efficiency of amplification in 5plex qPCR of each of the amplicons. As known in the art, a perfect qPCR would be assumed to double amount of amplicon (and hence also the net TAQMAN® fluorescence) per cycle, leaving an absolute direction coefficient of 1. In line with this, as shown in FIG. 4, the absolute direction coefficients for all amplicons except for the largest amplicon of 318 bp are 0.9 or higher, indicating a robust amplification close to doubling TAQMAN® probe degradation per PCR cycle. The largest amplicons size shows >0.8 absolute direction coefficient indicating that the largest fragment amplifies slower and that there is little point in designing a PCR QC test with longer amplicons for this type of TAQMAN® probe-based assay.

Example 2. Automated FFPE Sample Processing, Nucleic Acid Quality Assessment, Target Actionable Marker Screening, and Library Construction For the purpose of demonstrating the feasibility of the present invention, a set of Biocartis Idylla cartridges was prepared, each cartridge comprising in separate PCR chambers: (i) reagents for performing the above-described QC 5plex qPCR, (ii) reagents for performing target qPCR for detecting wt and V600M/R mutant BRAF, and (iii) reagents for constructing a DNA library compatible with Illumina MiSeq sequencer. Next, a set of FFPE samples to be analyzed on said cartridges were spiked with plasmids encoding for human BRAF. To simulate clinical reality, different BRAF sequences were used including a fragment containing a wild type (wt) BRAF sequence, a fragment encoding for a V600M mutation, and a fragment encoding for two mutations V600K and T149C. The two mutated fragments were spiked in different amounts with respect to the amount of the wild type copies present in the FFPE samples to obtain a relative concentration of 10% and 5%, respectively. Each of the different BRAF-spiked FFPE samples was introduced into a separate cartridge and processed in a fully automated manner on the Biocartis Idylla instrument. In brief, the processing involved sample liquefaction (as described in e.g. WO2014128129), followed by nucleic acid purification on a silica membrane provided in the cartridge, and then followed by three independent and individually-controlled PCR reactions performed in parallel, which included: (i) verification of the quality of the purified nucleic acids via quality control 5plex QC q PCR, as described above; (ii) real time detection of selected BRAF targets (qPCR for target actionable mutations); and (iii) construction of a DNA library using BRAF-specific or standard random-priming primers comprising linkers compatible with Illumina MiSeq sequencer. The latter library-construction PCR was performed using a Q5 high fidelity hot start polymerase (New England Biolabs) and cycled according to the following programme: 5' at 95° C. and 50 cycles of 90" at 60° C., 5" at 94° C.

Figure 5:
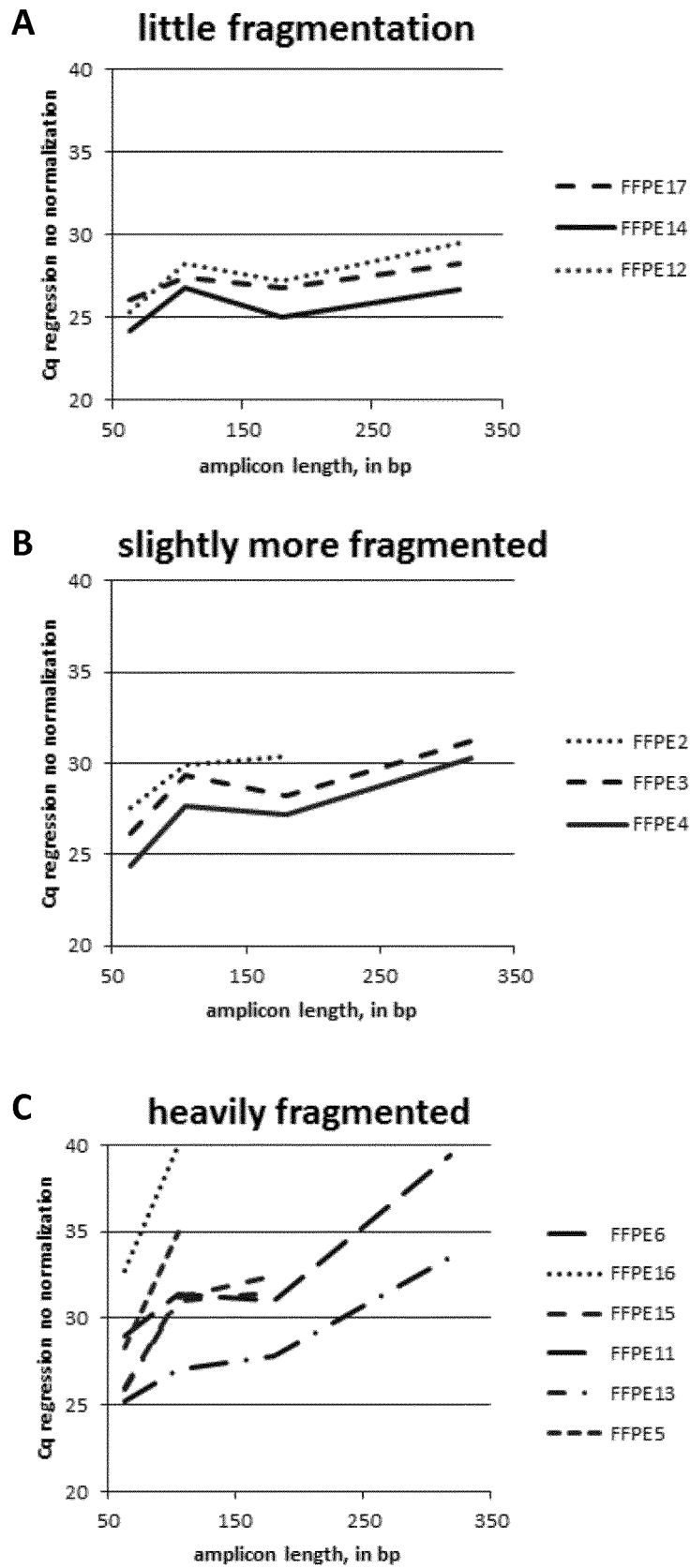
FIG. 5: shows the ability of the 5plex qPCR to distinguish between different degrees of nucleic acid fragmentation. Panel A shows results obtained from 3 FFPE samples having relatively intact DNA; Panel B shows results from another set of 3 FFPE samples with a higher level of fragmentation; lastly, Panel C shows results from 6 different FFPE samples containing heavily fragmented DNA.

FIG. 5 shows the results of the 5plex QC qPCR on the different FFPE samples, which provide information with regard to the integrity of the DNA present in said samples. Panel A shows three examples of FFPE tissue samples that contain relatively intact DNA. Panel B shows three other examples that have a slightly higher degree of DNA fragmentation. Lastly, Panel C shows 6 examples of FFPE tissue samples that contain heavily fragmented DNA, which is a counter-indication for subjecting such samples to further analysis by NGS.

Figure 6:
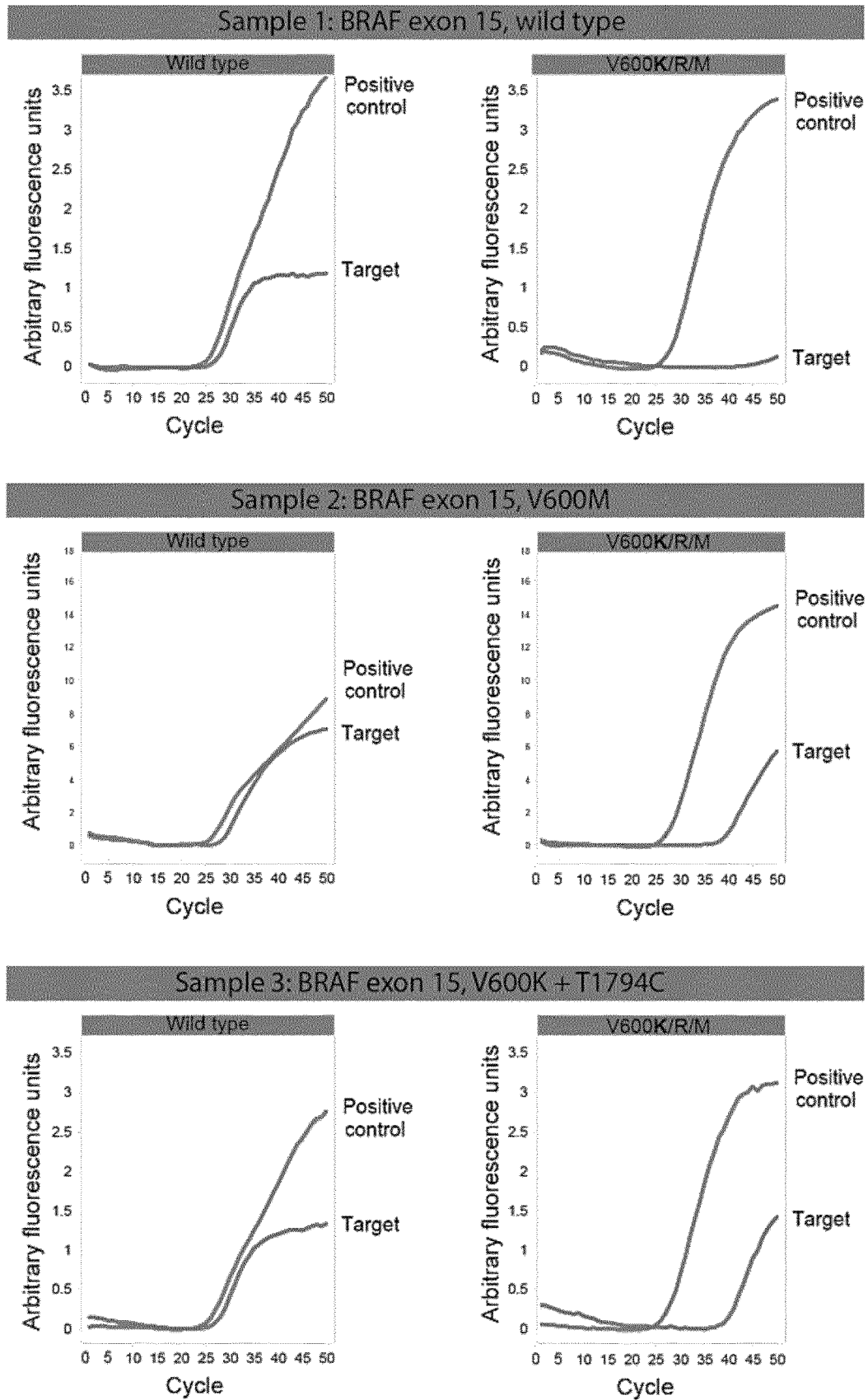
FIG. 6: shows results of a BRAF-specific qPCR capable of discerning between wt and V600K/R/M BRAF mutants, performed on three FFPE samples each spiked with a plasmid containing a sequence encoding for either wt BRAF, V600M mutant BRAF, or V600K and T149C double-mutant BRAF.

Based on the results of the 5plex QC qPCR, three samples with relatively intact DNA and containing three different forms of spiked BRAF (wt, V600M mutant, or double mutant V600K+T149C) were selected further investigation. Firstly, the results obtained from the assay qPCR capable of detecting wt BRAF and V600M BRAF mutation were checked to confirm the presence of the correct BRAF form. The results are shown in FIG. 6 They demonstrate that in all of the screened three FFPE samples, wt BRAF signal could be detected (FIG. 6, left column, the term "target" refers to wt BRAF sequence). This result was expected as all FFPE samples prior to spiking with different BRAF plasmids were known to contain wt genomic BRAF sequence. Concerning the detection of the V600M mutant (FIG. 6, right column, the term "target" refers to V600M/K BRAF sequence), as expected, in the sample spiked only with the wt BRAF-encoding plasmid, no V600M mutant could be detected (FIG. 6, top right pane; flat signal line for the target). However, in the FFPE samples spiked with either the V600M mutant, or the double mutant V600K+T149C, the mutation V600M was correctly detected at the expected amounts (FIG. 6, right column, bottom and middle pane). Because the used-herein BRAF-specific qPCR did not include a specific probe for the T1794C mutation, said mutation could not be detected in the double mutant BRAF-spiked sample.

Example 3. Sequencing of the Selected NGS Libraries

Figure 7:
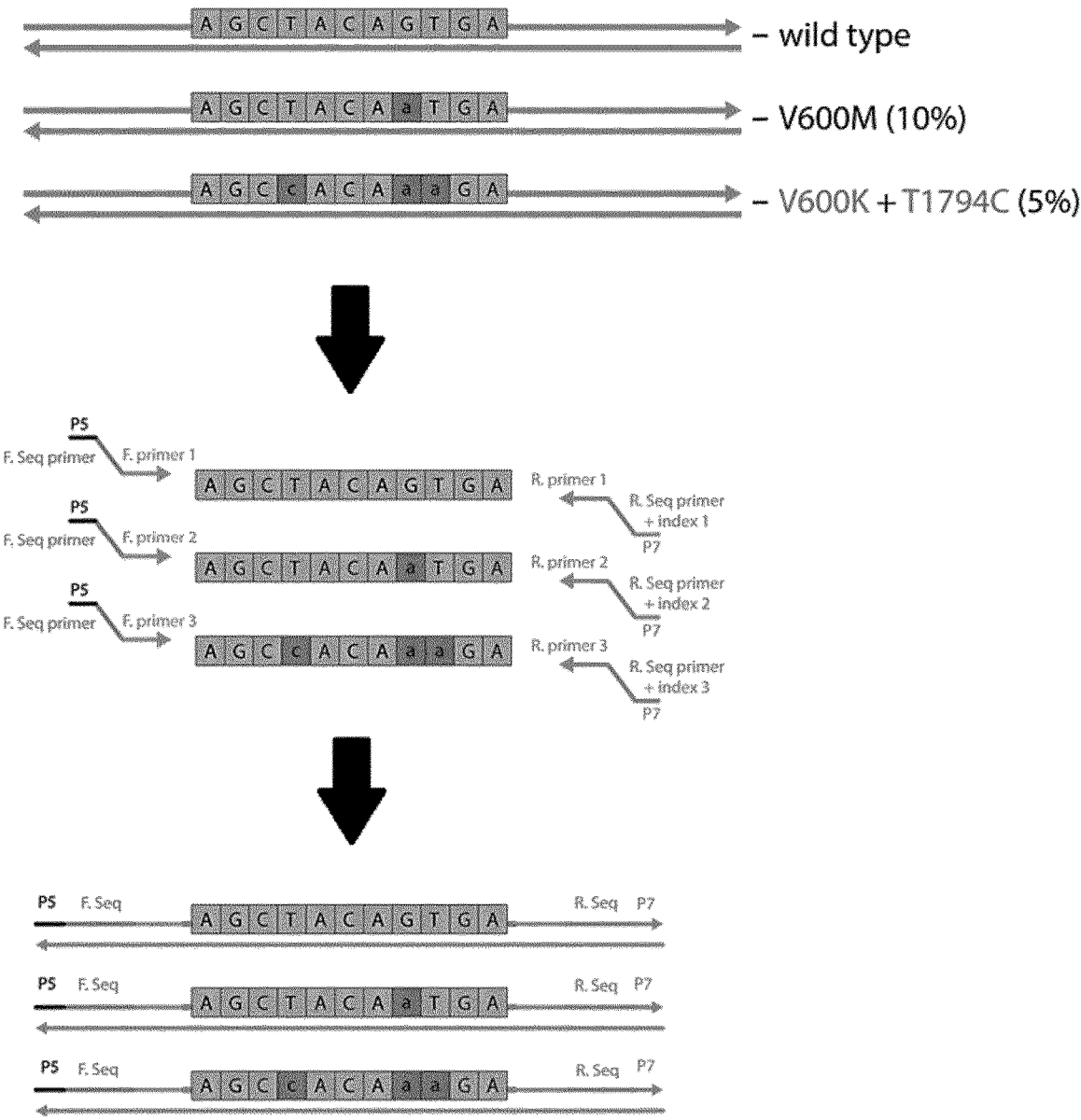
FIG. 7: shows principles of a one type of NGS-ready library preparation using library PCR with primers containing NGS-specific adapters. Sequences of wild type (SEQ ID NO: 1), V600M (SEQ ID NO: 2) and V600K+T1794C (SEQ ID NO: 3) are represented.

To confirm the results of the BRAF-specific qPCR and to also detect the presence of the undetected T1794C mutation, the NGS libraries constructed from the same three selected FFPE samples plasmid (wt, V600M, or V600K and T149C) were then subjected to Illumina MiSeq sequencing. The library PCR used for constructing these libraries is schematically shown in FIG. 7 and, as mentioned above, was performed on the same cartridges as and in parallel with the 5ples QC PCR and the BRAF-specific assay qPCR. The library PCR included 50 cycles and used simplified BRAF-specific fusion primers (also known as tailed primers). The fusion primers (shown in middle pane of FIG. 7) in addition to the target (BRAF)-specific sequence also contained sequencing primer sequence and a tag (P5 and P7) for flow cell attachment. In addition, the reverse primer also contained a barcode (or and index) that during a sequencing run allows to discern between samples obtained from different sources. The reason for introducing such barcode is that typically, libraries constructed from different samples or patients are pooled and sequenced on the same NGS instrument. Thus, in order to differentiate between libraries obtained from the three different FFPE samples, each cartridge contained a slightly different reverse primer having a unique barcode sequence.

Before sequencing, the three NGS libraries were recovered from respective cartridges using a needled syringe, after which the samples were pooled and purified further on the bench to remove any unreacted primers and primer-dimers. It should be noted that the latter purification step can also be performed automatically. Finally, the purified NGS-libraries were loaded into a flow cell of the MiSeq Illimina instrument and sequenced.

Figure 8:
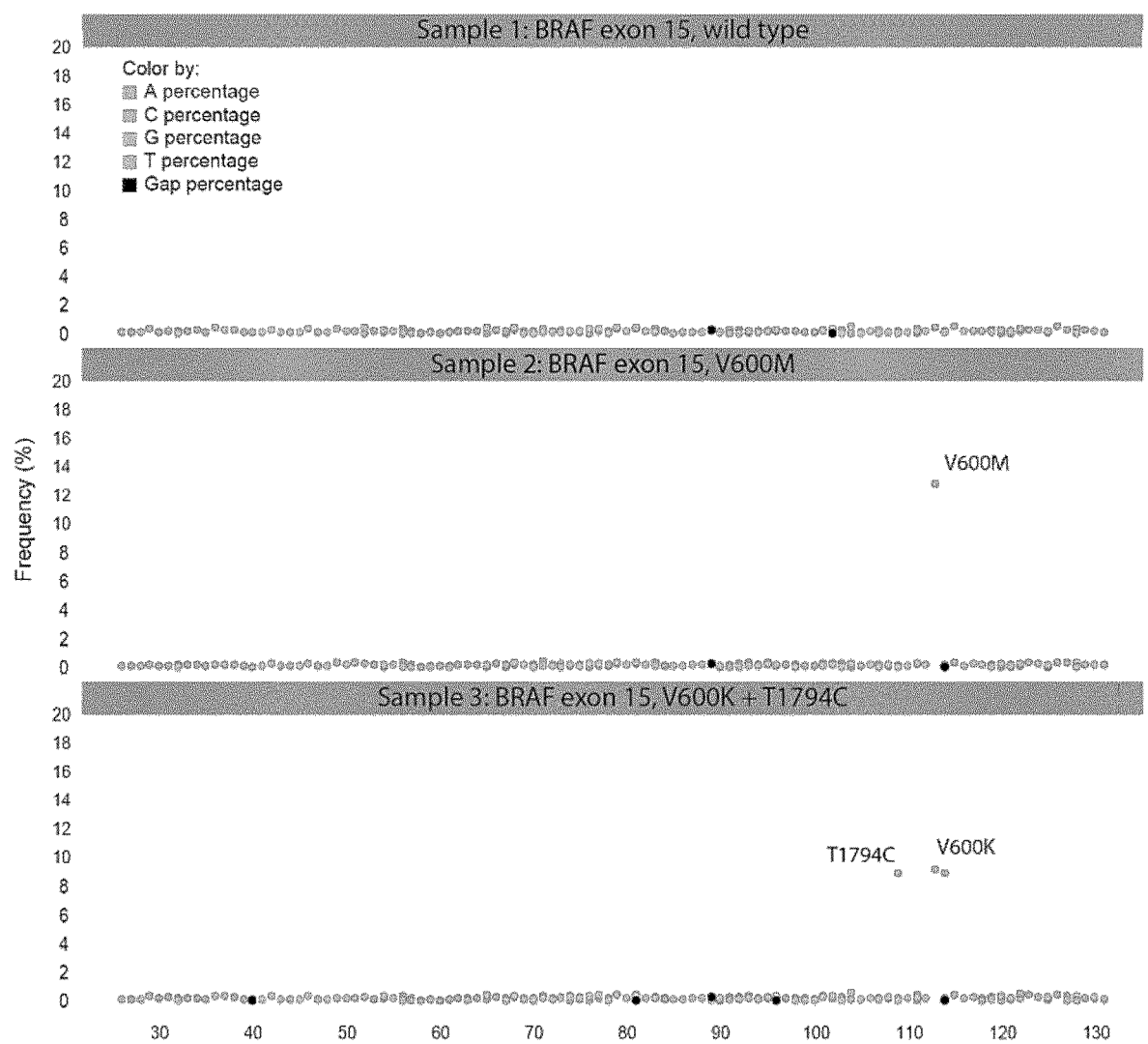
FIG. 8: shows results of NGS performed on three FFPE samples each spiked with a plasmid containing a sequence encoding for either wt BRAF, V600M mutant BRAF, or V600K and T149C double-mutant BRAF.

The results of the sequencing run are shown in FIG. 8. In line with the aforedescribed results of the BRAF-specific qPCR, in the first sample that contained only wt BRAF no mutations were detected. For the two other samples, all the expected BRAF gene mutations were correctly identified during sequencing, even if they could not be captured in the BRAF-specific qPCR. In particular, NGS not only detected the T1794C BRAF mutation missed on the target-specific qPCR, but also allowed to discriminate between the V600M and V600K mutations in mutant- and double mutant-spiked FFPE samples, respectively, thus providing even more exact identification of the already detected mutations. The present results demonstrate the unprecedented robustness of the present invention, wherein desired results are not only provided in a fast and efficient way, but also can be successfully followed up at will if deeper insight is desired.

Figure 9:
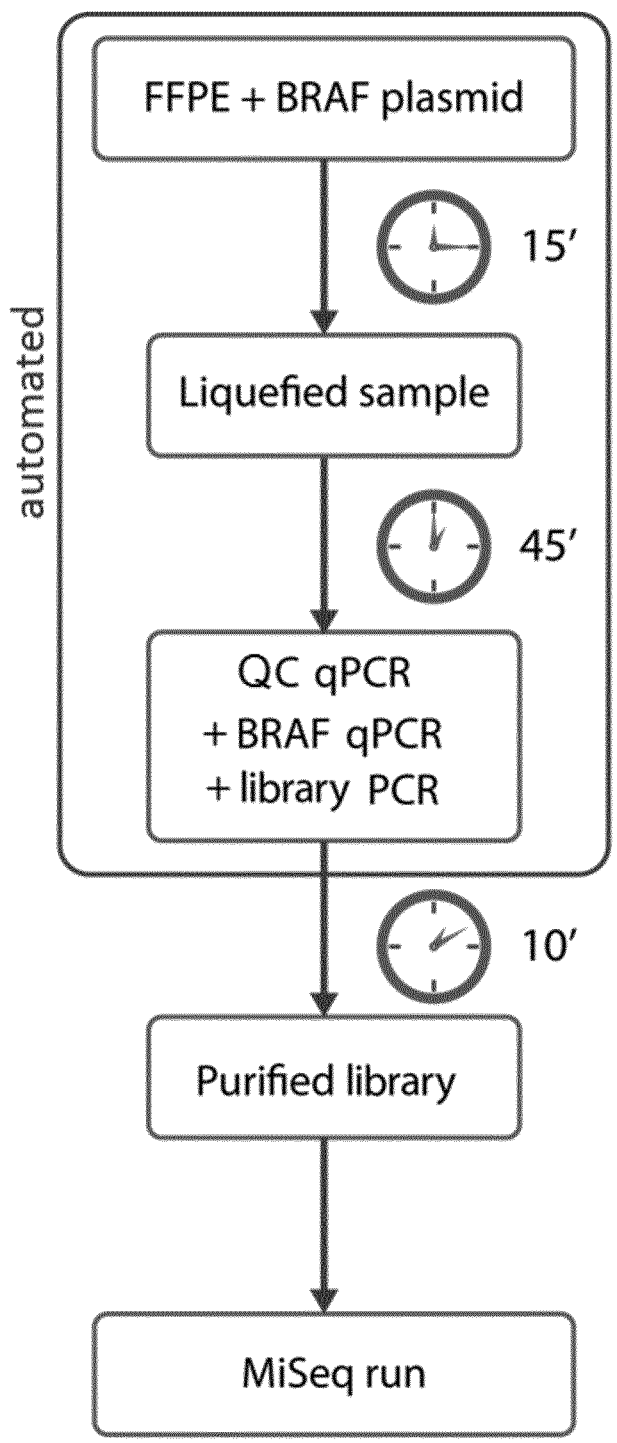
FIG. 9: shows an example of an optimized sample-to-result workflow according to the present invention.

For the fuller appreciation of the present invention, the above-described workflow is schematically illustrated in FIG. 9. It starts from providing an FFPE sample into a cartridge, after which the subsequent steps till obtaining of the final qPCR results (of both QC qPCR and target actionable marker qPCR, here BRAF) and ready-to-use library are performed in a fully automated and rapid manner (real time frames provided). It should be noted that all these results and the library are obtained from the same and identically-processed sample, which ensures high-comparability of the data from different assays. Notably, by concomitant NGS library construction and providing information with regard to said library's quality, the present approach not only allows to quickly subject a given sample to an NGS clinical follow-up, but also allows to decide whether such rather costly follow-up is feasible in view of that sample's quality. In view of the above, the present invention opens new possibilities in the current diagnostic practice.

The invention claimed is:

1. An automated system for quantitative PCR (qPCR) analysis of a nucleic acid present in a biological sample received into said system and for concomitant preparation of a sequencing nucleic acid library from said biological sample, the system comprising:

a cartridge; the cartridge comprising:

a) at least one sample-receiving compartment for receiving the biological sample, the sample-receiving compartment comprising a silica membrane and at least one additional reagent for liberating or purifying nucleic acid from the received biological sample;

b) a qPCR compartment in fluid connection with the sample-receiving compartment, the qPCR compartment suitable for amplifying nucleic acids and having a wall transparent to light allowing detection of signals generated during such amplification, said qPCR compartment comprising reagents for performing a multiplex quality control (QC) qPCR adapted to generate data suitable for assessing the quality of nucleic acid subjected thereto, wherein the reagents for performing the multiplex QC qPCR comprise at least two primer pairs designed for generating at least two amplicons of discernably different sizes, wherein the first one of the at least two primer pairs is adapted to generate an amplicon within the range from 50 to 110 bp, and wherein the second one of the at least two primer pairs is adapted to generate an amplicon within the range from 300 to 550 bp;

c) a library compartment in fluid connection with the sample-receiving compartment, the library compartment comprising reagents for preparing a sequencing nucleic acid library wherein said reagents for preparing a sequencing nucleic acid library comprise oligonucleotide adapters;

wherein the sample-receiving compartment, the qPCR compartment, and the library compartment are each comprised as separate compartments in the cartridge; and d) a mechanical arrangement for dividing the nucleic acid liberated or purified from said biological sample in the sample-receiving compartment between at least the qPCR compartment and the library compartment, wherein the qPCR compartment and the library compartment are both downstream of the sample-receiving compartment and are not in fluid connection with each other;

wherein the system is configured to run the multiplex QC qPCR and the nucleic acid library preparation simultaneously by individually and in parallel controlling thermocycling conditions at the qPCR compartment and at the library compartment, such that different thermocycling conditions may be used in the qPCR compartment and the library compartment;

and wherein the system is adapted to assess nucleic acid quality from the data obtained from said multiplex QC qPCR wherein the quality assessment comprises assessment of the degree of fragmentation of the nucleic acid.

2. An automated system according to claim 1, further comprising a second qPCR compartment suitable for amplifying nucleic acids and having a wall transparent to light allowing detection of signals generated during such amplification, said second qPCR compartment comprising target-specific primer pairs for performing non-quality control multiplex qPCR suitable for determining the presence or amount of genomic alterations potentially present in the nucleic acid subjected thereto.

3. An automated system according to claim 1, wherein the reagents for preparing a sequencing nucleic acid library further comprise reagents for generating nucleic acid fragments from the nucleic acid received into said library compartment and reagents for attaching the oligonucleotide adapters to one end, or both ends of the nucleic acid fragments.

4. An automated system according to claim 3, wherein the reagents for generating nucleic acid fragments comprise at least a primer and wherein the oligonucleotide adapters comprise a part of the at least a primer.

5. An automated system according to claim 1, said system further comprising a recovery compartment for recovering any of the following:

i) a part of the biological sample received into the automated system;

ii) a part of the nucleic acid liberated or purified in the automated system; and iii) at least a part of the sequencing nucleic acid library prepared in the automated system.

6. A method of performing qPCR with a concomitant preparation of a nucleic acid library on the automated system according to claim 1, said method comprising the steps of:

a) receiving a source of nucleic acid into the automated system;

b) liberating or purifying in said automated system the nucleic acid from at least a part of said received source of nucleic acid;

c) performing qPCR on the nucleic acid liberated or purified from the source of nucleic acid, said qPCR comprising thermocycling said nucleic acid in a thermocycling qPCR compartment comprised in said system and suitable for amplifying nucleic acids and allowing detection of signals generated during such amplification; and d) preparing a nucleic acid library in the library compartment comprised in said system;

wherein the steps c) and d) are performed on said automated system either sequentially or simultaneously.

7. The method according to claim 6, wherein the steps a) to d) are performed on said automated system on a cartridge.

8. An automated system for quantitative PCR (qPCR) analysis of a nucleic acid present in a biological sample received into said system and for concomitant preparation of a sequencing nucleic acid library from said biological sample, the system comprising:
a cartridge; the cartridge comprising:
a) at least one sample-receiving compartment for receiving the biological sample, the sample-receiving compartment comprising a silica membrane and at least one additional reagent for liberating or purifying nucleic acid from the received biological sample;
b) a qPCR compartment in fluid connection with the sample-receiving compartment, the qPCR compartment suitable for amplifying nucleic acids and having a wall transparent to light allowing detection of signals generated during such amplification, said qPCR compartment comprising reagents for performing a first multiplex quality control (QC) qPCR adapted to generate data suitable for assessing the quality of nucleic acid subjected thereto,
wherein the reagents for performing the multiplex QC qPCR comprise at least two primer pairs designed for generating at least two amplicons of discernably different sizes,
wherein the first one of the at least two primer pairs is adapted to generate an amplicon within the range from 50 to 110 bp, and wherein the second one of the at least two primer pairs is adapted to generate an amplicon within the range from 300 to 550 bp; and
c) a library compartment in fluid connection with the sample-receiving compartment, the library compartment comprising reagents for preparing a sequencing nucleic acid library wherein said reagents for preparing a sequencing nucleic acid library comprise oligonucleotide adapters; and
wherein the sample-receiving compartment, the qPCR compartment, and the library compartment are each comprised as separate compartments in the cartridge;
d) a mechanical arrangement for dividing the nucleic acid liberated or purified from said biological sample in the sample-receiving compartment between at least the qPCR compartment and the library compartment, wherein the qPCR compartment and the library compartment are both downstream of the sample-receiving compartment; and
e) a fluid channel configured to transfer at least a part of the sequencing nucleic acid library prepared from the library compartment to the qPCR compartment;
wherein the system is configured to run the first multiplex QC qPCR and the nucleic acid library preparation simultaneously by individually and in parallel controlling thermocycling conditions at the qPCR compartment and at the library compartment, such that different thermocycling conditions may be used in the qPCR compartment and the library compartment;
wherein the system is configured to run a second multiplex QC qPCR on the sequencing nucleic acid library;
and wherein the system is adapted to assess nucleic acid quality from the data obtained from said first and second multiplex QC qPCRs wherein the quality assessment comprises assessment of the degree of fragmentation of the nucleic acid.

* * * * *

SEQUENCE LISTING

<160> NUMBER OF SEQ ID NOS: 3

<210> SEQ ID NO 1
<211> LENGTH: 11
<212> TYPE: DNA
<213> ORGANISM: Artificial Sequence
<220> FEATURE:
<223> OTHER INFORMATION: Partial sequence encoding wild-type human BRAF
      protein

<400> SEQUENCE: 1
agctacagtg a                                                          11

<210> SEQ ID NO 2
<211> LENGTH: 11
<212> TYPE: DNA
<213> ORGANISM: Artificial Sequence
<220> FEATURE:
<223> OTHER INFORMATION: Partial sequence encoding mutant form of human
      BRAF protein having a V600M amino acid substitution

<400> SEQUENCE: 2
agctacaatg a                                                          11

<210> SEQ ID NO 3
<211> LENGTH: 11
<212> TYPE: DNA

```
<213> ORGANISM: Artificial Sequence
<220> FEATURE:
<223> OTHER INFORMATION: Partical sequence encoding mutant form of
      human BRAF protein having a T1794C transition and having a
      V600K amino acid substitution

<400> SEQUENCE: 3
agccacaaag a                                                           11
```